United States Patent
Alkadi et al.

(10) Patent No.: US 11,649,782 B2
(45) Date of Patent: May 16, 2023

(54) GAS EMISSION MONITORING AND DETECTION

(71) Applicant: Baker Hughes Oilfield Operations LLC, Houston, TX (US)

(72) Inventors: Nasr Alkadi, Oklahoma City, OK (US); Ammar Abdilghanie Mohammed, Oklahoma City, OK (US); Mahendra Joshi, Houston, TX (US); Bilal Zoghbi, Oklahoma City, OK (US); Valeria Di Filippo, Houston, TX (US); Pejman Kazempoor, Oklahoma City, OK (US); Jianmin Zhang, Houston, TX (US)

(73) Assignee: Baker Hughes Oilfield Operations LLC, Houston, TX (US)

(*) Notice: Subject to any disclaimer, the term of this patent is extended or adjusted under 35 U.S.C. 154(b) by 473 days.

(21) Appl. No.: 16/900,344

(22) Filed: Jun. 12, 2020

(65) Prior Publication Data

US 2021/0017926 A1 Jan. 21, 2021

Related U.S. Application Data

(60) Provisional application No. 62/874,755, filed on Jul. 16, 2019.

(51) Int. Cl.
*F01N 11/00* (2006.01)
*F02D 41/22* (2006.01)
(Continued)

(52) U.S. Cl.
CPC ........... *F02D 41/22* (2013.01); *F01N 11/007* (2013.01); *G01M 3/007* (2013.01); *G01N 21/3504* (2013.01); *G07C 5/006* (2013.01); *G07C 5/0816* (2013.01); *F02D 2041/225* (2013.01); *G01N 33/0004* (2013.01)

(58) Field of Classification Search
CPC ...... F02D 41/22; F02D 41/225; G01M 3/007; G01M 3/2807; G01N 21/3504; G01N 33/0004
USPC ........ 73/1.06, 23.31; 702/2, 22–35, 51, 104, 702/127, 188
See application file for complete search history.

(56) References Cited

U.S. PATENT DOCUMENTS 9,599,597 B1 * 3/2017 Steele .................... G01M 3/04
10,330,555 B1 * 6/2019 Tan ......................... G01M 3/00
(Continued)

FOREIGN PATENT DOCUMENTS

EP 3460424 A1 * 3/2019
KR 101799119 B1 * 11/2017

*Primary Examiner* — Jeffrey P Aiello
(74) *Attorney, Agent, or Firm* — Mintz Levin Cohn Ferris Glovsky and Popeo, PC

(57) ABSTRACT

Systems, methods, and a computer readable medium are provided for monitoring and detecting a gas emission. Sensor data including gas concentration and wind data associated with a gas emission from an emission source is received from Near-Field and Far-Field sensors configured within a gas production and distribution environment. The sensor data can be provided as inputs to a Near-Field dispersion model to determine an emission rate associated with the gas emission and one or more source locations associated with the gas emission. The emission rate can be included in emission data and provided for output. Related apparatus, systems, techniques, and articles are also described.

20 Claims, 8 Drawing Sheets

(51) Int. Cl.
  *G07C 5/00* (2006.01)
  *G07C 5/08* (2006.01)
  *G01M 3/00* (2006.01)
  *G01N 21/3504* (2014.01)
  *G01N 33/00* (2006.01)

(56) References Cited

U.S. PATENT DOCUMENTS

| | | | |
|---|---|---|---|
| 10,962,437 B1* | 3/2021 | Nottrott | G01N 21/3504 |
| 2004/0149579 A1* | 8/2004 | Palmer | G01N 33/0027 |
| | | | 204/431 |
| 2017/0193790 A1* | 7/2017 | Cornwall | G01M 3/00 |
| 2019/0137388 A1* | 5/2019 | Mallery | G01J 5/0806 |

* cited by examiner

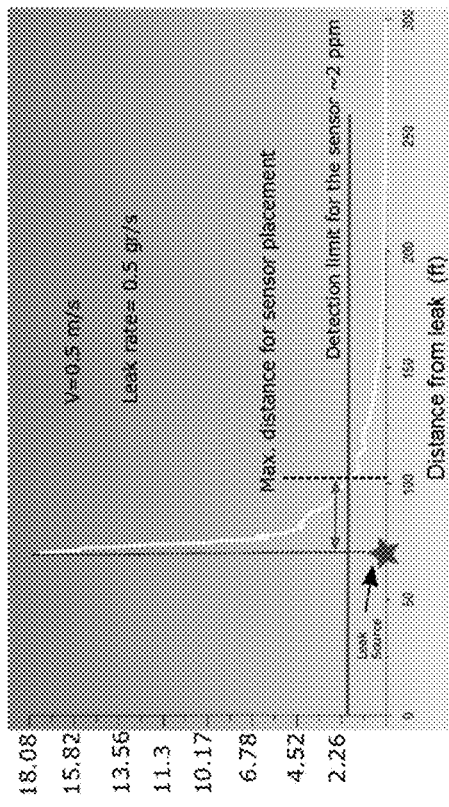
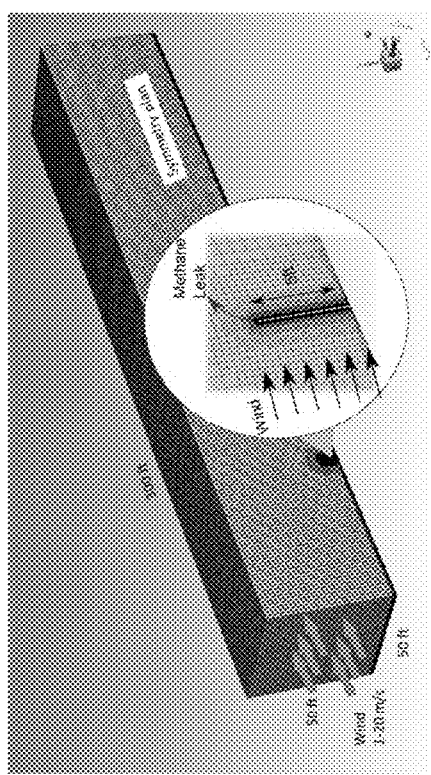
Figure 1C
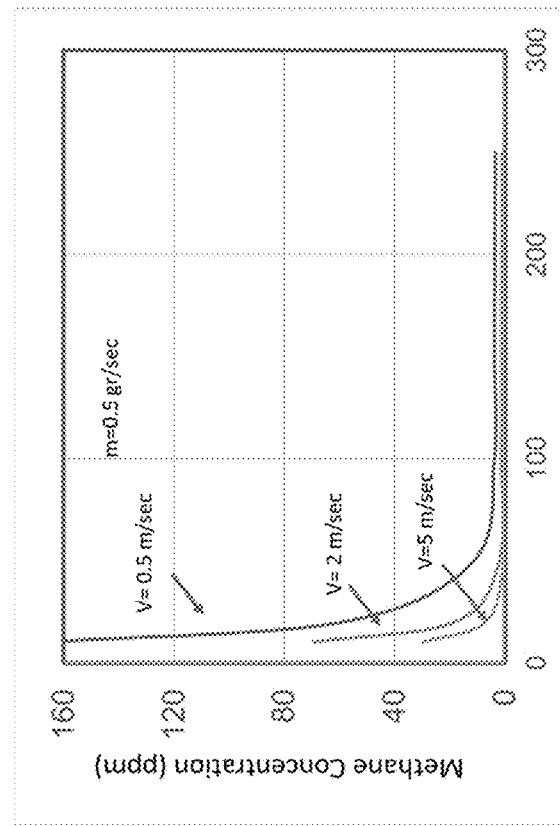
Figure 1D
Figure 1E

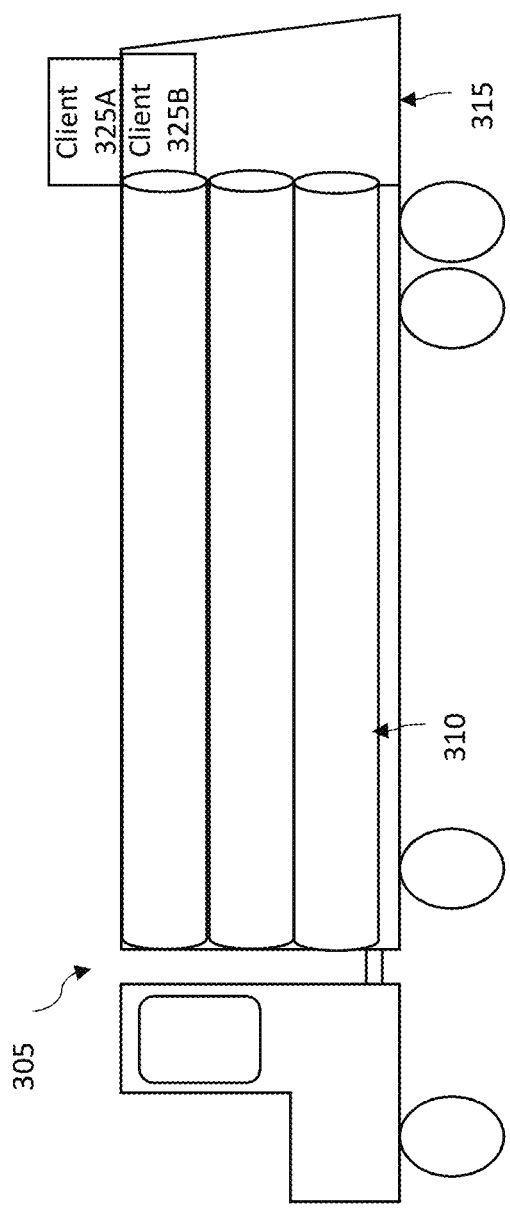
Figure 3A
Figure 3B
Figure 3C

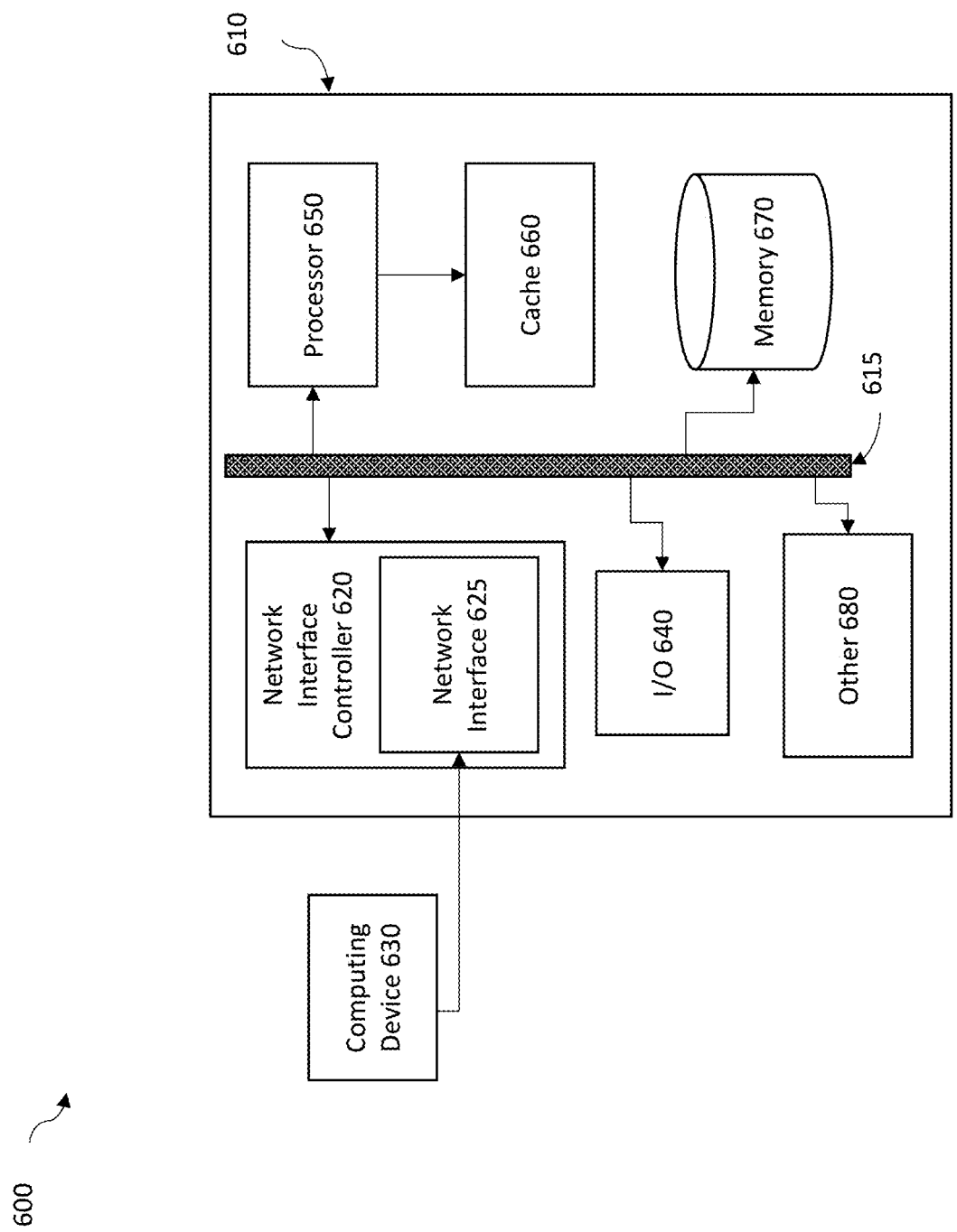

GAS EMISSION MONITORING AND DETECTION

RELATED APPLICATION

This application claims priority under 35 U.S.C. § 119(e) to U.S. Provisional Application No. 62/874,755 filed Jul. 16, 2019, the entire contents of which are hereby expressly incorporated by reference herein.

BACKGROUND

Monitoring and detection of gas leaks is commonly performed by inspection of industrial assets, such as assets configured in gas production and distribution environment. Inspections can be performed to ensure operational safety of the assets and to determine the presence of leaks or gas emissions which can be emanating from an emission source. Gas leaks in these environments can create hazardous operating conditions for personnel assigned to operate, maintain, and repair the industrial assets and can reduce production rates. Gas leaks can occur as a result of equipment failures which can cause the release of unplanned, or fugitive gaseous emission. Gas leaks can also occur as a result of venting that is part of the normal and expected operation of the equipment or assets. Localized weather patterns can alter the concentration, location, and distribution of the gas emission making it difficult to accurately determine an emission source associated with the gas leak.

SUMMARY

In one aspect, methods are provided. In one embodiment, the method can include receiving Near-Field sensor data and Far-Field sensor data from one or more sensors configured with respect to a gas production and distribution environment. The sensor data can be associated with a gas being emitted from an emission source. The method can also include filtering the received sensor data. The method can further include determining gas concentration data associated with the gas emission. The method can include determining an emission rate corresponding to the gas emission. The method can also include generating emission data corresponding to the gas emission. The emission data can include the determined emission rate and one or more source locations associated with the gas emission. The method can further include providing the emission data.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

DESCRIPTION OF DRAWINGS

These and other features will be more readily understood from the following detailed description taken in conjunction with the accompanying drawings, in which:

FIGS. 1C-1E are diagrams illustrating an exemplary process for selecting client grid dimensions using the system for monitoring and detecting gas emissions;

FIGS. 3A-3C are block diagrams illustrating one exemplary embodiment of a mobile platform including for use in in a system for monitoring and detecting gas emissions;

FIG. 6 is a block diagram of an exemplary computing device in accordance with an illustrative implementation of the gas monitoring and detection system of FIGS. 1 and 4.

Figure 1A:
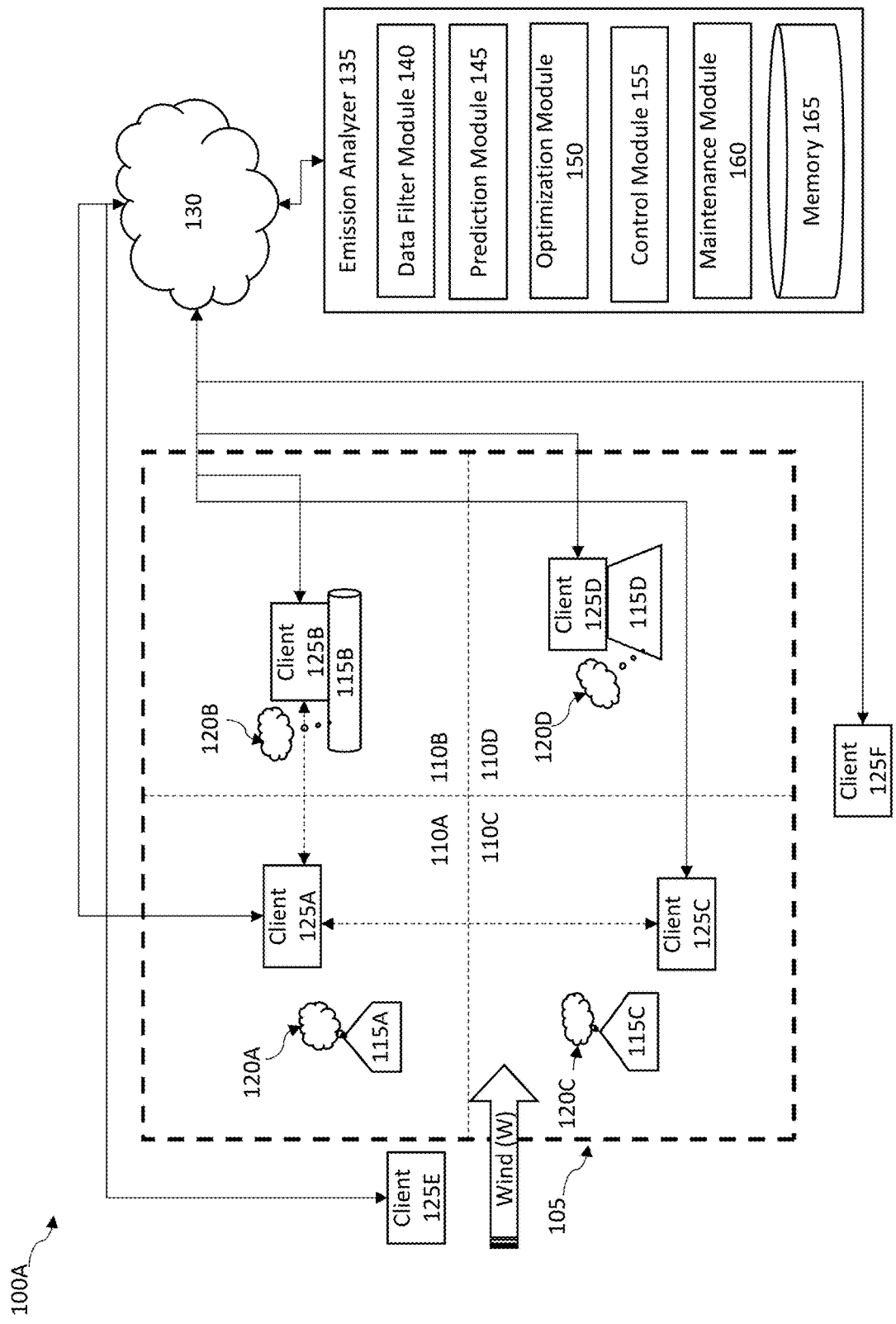
FIG. 1A is a block diagram illustrating one example of a system for monitoring and detecting gas emissions.

It is noted that the drawings are not necessarily to scale. The drawings are intended to depict only typical aspects of the subject matter disclosed herein, and therefore should not be considered as limiting the scope of the disclosure.

DETAILED DESCRIPTION

Gas production and distribution environments include networks of pipelines coupling industrial assets, such as motors, compressors, separators, and accumulation tanks, used to store, process, and distribute gas throughout the production and distribution environment. The various industrial assets can be an emission source of a gas that may be released into the atmosphere. Operators of these environments perform monitoring and inspection of the pipelines and industrial assets to detect leaks or emissions which may be released during failure of an industrial asset and may cause unsafe operating conditions or reduce operating production rates. Operators also perform monitoring and inspection of the pipelines and industrial assets to ensure venting of gases are occurring in accordance with the expected and normal operational characteristics.

Methane leak detection is one of the pressing needs in the oil and gas industry today. Determining the location, type of emission source, and rate of emission can be a time-consuming, error prone process. The process can be further complicated by the presence of prevailing seasonal wind or weather conditions which may distribute the gas emission in a manner which can make determining emission locations, sources, and rates challenging.

Current emission assessment methods can include emission monitoring which may be required by law for the day-to-day operation of a gas production and distribution environment. Emission monitoring in a continuous manner can yield emission estimates with uncertainties in the range of +/−5% provided sensors are installed in close proximity to all (known) leak sources. In practice, it is cost prohibitive to install dedicated sensors at every component and every equipment that has a potential to emit depending on equipment failure or venting as a part of normal operation. In addition, there is a lack of commercially available emission monitoring systems employing leak analysis methods to accurately determine individual leak rates based on type of equipment (vessels, compressors, pipe seals and flanges, valves, actuators, manifolds, etc.) and pinpointing the leak sources and their locations under prevailing wind conditions. Current emission assessment methods can also include emission source simulation. Computer models are available for estimating emissions from some types of emission sources. These models apply empirical correlations and/or fundamental engineering principles to develop rigorous emission estimates based on the specific operating and design parameters of the emission source. Simulators offer the ability to accurately predict emissions from sources within +/−25% uncertainty, however they require more time, effort, user knowledge, and input data to generate emission rate estimates. In addition, the simulation models require inputs of the specific emission source design and operating input data which can be difficult to obtain. Another current method of estimating emission rates can include statistical approached in which emission factors are determined for the average emission from a group of sources is related to an appropriate activity. However, the use of emission factors is often an oversimplification and subject to even higher uncertainties compared to the prior two methods mentioned above. Although the method becomes a statistically valid approach when considering aggregate emission from a large number of sources, it is less useful when applied for determining an emission rate for a single emission source.

An improved gas emission monitoring and detection system can be configured to receive sensor data from Near-Field and Far-Field sensors which are strategically deployed at predetermined locations throughout a gas production and distribution environment and to determine an emission rate associated with an emission leak emanating from an emission source or periodic vent gas emissions associated with specific equipment. The sensors can be deployed in a grid-like arrangement and can be configured to communicate data with each other. Further, the grid spatial dimensions (X and Y) are predetermined based on minimum threshold detection level of sensors under the prevailing wind velocity range observed for the region and diffusion/advection of gas plume relative to outermost sensors. The received sensor data can include wind data associated with the prevailing or current weather conditions as well as gas concentration data corresponding to an emission source in proximity of the Near-Field or Far-Field sensor. The collection of sensor data can be configured with respect to weather forecasting data received from a public or private weather forecasting source so as to coordinate sensor data collection during weather conditions which are least likely to introduce noise in the received sensor data signals. The emission rate can be determined using a plume advection-diffusion model which can receive the sensed gas concentration data and the wind data as inputs to determine an emission rate associated with a particular emission source. The emission rate can be included in emission data generated by the improved gas monitoring and detection system described herein.

The improved gas monitoring and detection system can thus automate the otherwise manually intensive tasks of manually monitoring and detecting emission sources for leaks and determining emission rates. Such an improved gas monitoring and detection system can provide gas production and distribution operators with greater insight into the current operating conditions of the industrial assets configured in the gas production and distribution environment and can also aid in identifying gas emission locations to aid maintenance and repair operations based on early detection of leaks. The improved gas detection and monitoring system can generate emission data, including emission rates and locations of emission sources, to assist operators in planning configurations of industrial assets and deployment of monitoring and inspection personnel or equipment, while maintaining production at acceptable and profitable levels.

Embodiments of systems and corresponding methods for generating emission data based on sensor data associated with a plume of gas emanating from an industrial asset configured in a gas production and distribution environment are discussed herein. However, embodiments of the disclosure can be employed for generating emission data based on sensor data associated with other types of assets or other sources of gas which are not associated with a gas production and distribution environment without limit.

FIG. 1 is a block diagram illustrating one example of an architecture 100A of a system for monitoring and detecting gas emissions. The architecture 100A includes a gas production and distribution environment 105 which has been divided into four quadrants, e.g., quadrants 110A-110D. The gas production and distribution environment 105 also includes a number of emission sources 115, such as equipment or assets which may be sources of a gas leak or emission 120. The architecture 100A also includes a number of clients 125, which can include one or more sensors which can be configured to detect sensor data corresponding to the localized wind conditions, e.g., W. For example, as shown in FIG. 1, the wind, W, is blowing across the gas production and distribution environment 105 from the left side of FIG. 1, to the right side of FIG. 1. The clients 125 can also include one or more sensors which can be configured to detect sensor data associated with the gas emissions or leaks 120. The clients 125 can be configured to provide the sensor data via a network 130 to the emission analyzer 135. The emission analyzer 135 can be configured with a data filter module 140, a prediction module 145, an optimization module 150, a control module 155, a maintenance module 160, and/or a memory 165. The emission analyzer 135 and the modules configured therein can receive the sensor data from one or more clients 125 and can generate emission data used in determining a gas emission or leak from one or more gas sources 115.

As shown in FIG. 1, the architecture 100A includes a gas production and distribution environment 105. The gas production and distribution environment 105 can occupy a geographic location that can be configured into a grid of quadrants 110. In some embodiments, any of the quadrants 110 can be associated with an area of arbitrary dimensions and shape. The quadrants 110 can be identifiable by an identifier, label, or other similar means which can be used to identify the location of any emission sources 115, emissions 120, and/or clients 125 which may be present within the quadrants 110. In some embodiments, the gas production and distribution environment 105 can be configured in a rural, urban, or suburban environment. For example, the gas detection and monitoring system described herein can be configured for use in a city wherein a number of clients 125 can be configured with respect to existing infrastructure elements, such as light poles, street lights, public safety and communication devices, as well as buildings or other structures which may be present within the city. In these examples, the clients 125 can be distributed throughout the city and configured to detect gas emissions which may be As further shown in FIG. 1, a number of emission sources 115 can be present within the gas production and distribution environment 105. In some embodiments, one or more of the emission sources 115 can be located outside of the gas production and distribution environment. The emission sources 115 can include equipment associated with the production and distribution of a gas. For example, the emission sources 115 can include a compressor, a separator, a pump, a storage tank, a valve, an actuator, and/or one or more components of an emission source 115. Additional examples of emission sources 115 can include a piping components such as flanges, pipe seals such as gaskets, O-rings, dynamic seals for integral engine/compressor, such as cross piece, actuator vents, flares, burners and fuel piping, boilers, heaters, gas storage vessels, dehydration units, sour gas treating units, cryogenic gas treatment units, heat exchangers, etc. In some embodiments, the emission source 115 can be one or more storage tanks configured on a mobile platform such as a transport truck configured to carry liquid natural gas (LNG), and/or compressed natural gas (CNG).

The emission sources 115 can emit or leak gas 120 into the environment as a result of normal, required, and expected operating conditions of the emission source 115, such as venting of a compressor overflow line, or as a result of unexpected, abnormal operating conditions for which routine venting or gas emission is not required, such as a failure of a valve configured on a separator. Gas emissions 120 occurring during unexpected, anomalous operating conditions can be referred to as fugitive emissions and can reflect gas emissions that have escaped the operating equipment used to contain the gas for production and/or distribution operations. Fugitive gas emissions 120 can be caused by failures of a seal, gasket, surface, flange or the like that is associated with an emission source 115. In some embodiments, gas emissions 120 can occur as a result of corrosion, vibration, electrical or mechanical failures which may be present with respect to the emission source 115. Gas emissions 120 can include common gas species such as methane, ethane, propane, butane, hexane, and other hydrocarbons such as natural gas liquids (C5, C6, C8-10), mixtures of alkanes, sour gases include H2S, SOx, carbon disulfide, unsaturated HCs/petrochemicals such as ethylene, propylene, or the like which can be emitted from various emission sources 115 and/or detected via clients 125.

As shown in FIG. 1, a number of client 125 can be configured with respect to the gas production and distribution environment 105. The clients 125 can include a computing device, including a processor, one or more sensors, and a memory storing executable instructions configured to cause the sensors to generate sensor data associated with weather conditions, such as a wind velocity associated with the wind (W), and/or a gas emission 120. The clients 125 can be arranged in proximity to an emission source 115 or a potential emission source 115. In some embodiments, the clients can be configured on a mobile platform, such as a CNG or LNG transport truck. In this way, the clients 125 can be configured to generate and transmit sensor data associated with the current weather conditions and a gas emission 120 that may be emanating from a gas emission source 115.

For example, as shown in FIG. 1, in quadrant 110A, the client 125A has been configured with respect to an emission source 115A which may be a potential emission source for a fugitive gas emission 120A, such as a compressor. The client 125A may be positioned with respect to the potential emission source 115A and prevailing weather conditions, such as the wind, W, such that it is most likely to detect the gas emission 115A and generate sensor data corresponding to the gas emission 115A. Similarly, in quadrant 110C, client 125C may also be configured with respect to emission source 115C which may also be a potential emission source for a fugitive gas emission 120C, for example, a gas emanating from a flange or coupling of a separator which has experienced a failure and is exhibiting anomalous operating conditions. Clients 125A and 125C can be configured as Far-Field sensors which can be positioned 30 to 100 feet away from potential emission sources 115A and 115C, respectively. In some embodiments, the Far-Field sensors can be positioned 10 to 100 feet, or 50 to 200 feet from the potential emission source 115. In some embodiments, the Far-Field sensors can be positioned 4 to 8 feet above the surface of the ground. The Far-Field sensors can be positioned on the periphery of the gas production and distribution environment 105, as shown by client 125E. In some embodiments, the client 125E can be configured as a remote weather station capable of transmitting weather data to another of clients 125 or to the emission analyzer 135. The Far-Field sensors, clients 125A, 125C, and/or 125E, can be preferably positioned to maximize detection of gas emissions based on the direction of the seasonally prevailing wind conditions (W).

In quadrant 110B, client 125B can be configured with respect to emission source 115B, such as a vent associated with a compressor. The emission source 115B vents gas as part of the normal operating behavior of the compressor. Thus, the absence or sudden change in the gas emission 120B may indicate a failure of the emission source 115B (e.g., the vent), or the equipment associated with the emission source, such as the compressor. The client 125B can be configured as a Near-Field sensor to detect the gas 120B emanating from the emission source 115B. As a Near-Field sensor, client 125B can be positioned in proximity to a potential emission source 115B. For example, the client 125B can be placed less than 1 foot away, less than 2 feet away, or less than 5 feet away from the potential emission source 115B. In some embodiments, the Near-Field sensor, client 125B, can be positioned with respect to an emission source 115B, which can be operating under high operational pressures. In some embodiments, the Near-Field sensor or client 125B, can be configured with an arrangement of baffles in order to minimize the advection-diffusion effect of the local wind conditions, W. Similarly, in quadrant 110D, client 125D can be configured as a Near-Field sensor in proximity with emission source 115D. For example, emission source 115D can be a high-pressure, methane storage system that is configured to routinely vent excess methane 120D from the storage system. In this example, the client 125D can include a Near-Field sensor configured to monitor and detect the methane emission 120D. Additionally, client 125F can be configured as a Near-Field sensor that can be deployed on a mobile platform, such as a transport truck used to carry and distribute CNG or LNG gas. The Near-Field sensor configured as client 125F can be positioned with respect to the mobile platform so as to monitor and detect a gas leak that may emanate from one or more of the gas transport devices included in the mobile platform. Additional details regarding the configuration of Near-Field sensors with respect to mobile platforms will be provided in relation to FIG. 3.

As shown in FIG. 1, the clients 125 can be configured to share data with other clients 125. For example, as shown in FIG. 1 by dashed lines between clients 125A and 125 C and between clients 125A and 125B, the clients 125 can transmit and receive data with other clients 125 so as to form a sensor grid, a network of clients 125, or the like. The clients 125 can further be operatively coupled via a network 130 to an emission analyzer 135. The emission analyzer 135 can receive the sensor data from clients 125 as Near-Field sensor data, such as from clients 125B, 125D, and/or 125F. In addition, the emission analyzer 135 can receive the sensor data from clients 125 as Far-Field sensor data, such as from clients 125A, 125C, or 125E. The emission analyzer 135 can be configured as a client computing device, or as a server computing device. In some embodiments, one or more of the modules can be located remotely from the location of the emission analyzer 135. The emission analyzer 135 can perform different processing functions in regard to gas emission monitoring and detection. For example, the emission analyzer can include a data filter module 140 configured to receive sensor and/or weather data and to detect parser errors, incorrect or anomalous data values, dates, or sensor measurements. In some embodiments, the data filter module can apply global mining to filter out data that lies outside of a sensor calibration data range associated with at least one of the clients 125. The emission analyzer 135 can also include a prediction module 145 configured to predict an emission rate for a particular gas emission 120 based gas concentration data converted from the filtered sensor data. The emission analyzer 135 can also include an optimization module 150 configured to perform data-driven modeling, machine learning, and statistical analysis of the gas emission 120. In some embodiments, the optimization module 150 can be configured in a machine learning process to perform the data-drive modeling and statistical analysis of the gas emission 120. The emission analyzer 135 can also include a control module 155 which can be configured to control one or more emission sources 115 or components associated the with emission sources 1115. In the event of determining anomalous venting or fugitive gas emissions 120, the control module 155 can execute instructions to control the operating parameters of the emission sources 115 via client 125. The emission analyzer 135 can further include a maintenance module 160 which can be configured to request, manage, and allocate maintenance and repair personnel in response to anomalous venting or fugitive gas emissions 120. For example, based on determining that rate of gas from emission source 115A is outside of the normal operating conditions, the emission analyzer 135 can execute instructions causing the maintenance module to provide emission data regarding the anomalous behavior of emission source 115A to maintenance personnel associated with the gas production and distribution environment 105 in order for corrective action to be applied to the emission particular emission source.

Figure 1B:
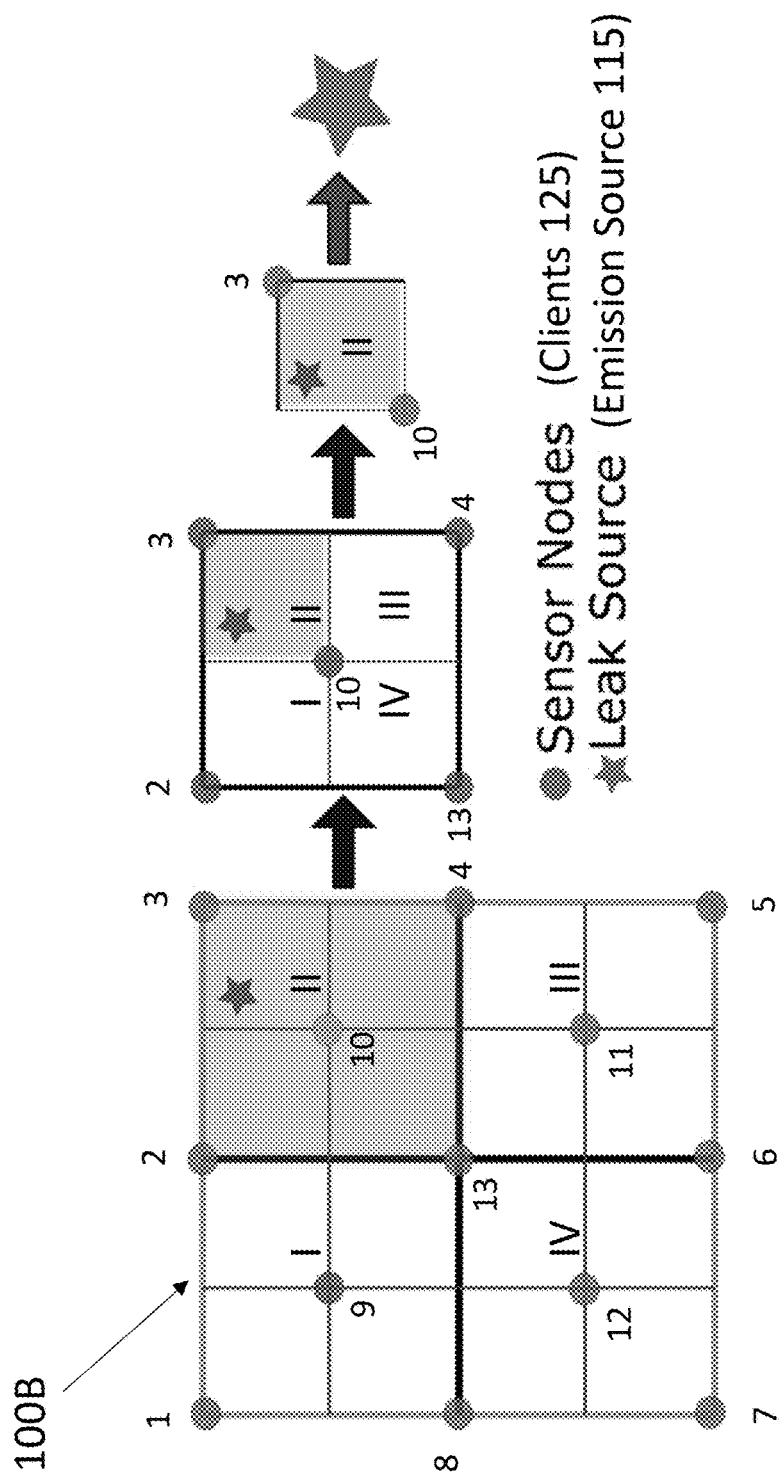
FIG. 1B is a diagram illustrating one example of a client grid of Near-Field and Far-Field sensors for use in a system for monitoring and detecting gas emissions.

FIG. 1B illustrates an example of Far-Field and Near-Field sensors as a client grid 100B where each sensor node is denoted by 1 through 13. The emission source 115 or leak source is shown at one location within the client grid as a star shaped icon. In one embodiment, the client grid is divided into four quadrants (I-IV). The Emission analyzer 135 will determine emissions under prevailing wind conditions for each sensor node and based on magnitude of emissions for each sensor node, it will select nodes 2, 3, 4, 13, and 10 being closest to the emission source 115 (the star icon) for various wind conditions. The next step would be to further collect data for the quadrant II and subdividing this quadrant into four quadrants (I-IV). Based on additional client data from nodes 2, 3, 4, 13 and 10, nodes 3 and 10 are selected as closest to the emission source 115. The next step is to select the quadrant II with client nodes as 3 and 10 in the closest vicinity of emission source 115 and also to estimate the leak rate based on diffusion/advection under prevailing wind conditions. This process of creating a client grid of certain dimensions (X, Y, Z) containing the emission source 115 and then using a process of elimination to first eliminate quadrants followed by eliminating client nodes 125 indicating zero or negligible emissions can be used to provide a structured approach to detecting the rate and location of leaks from emission sources 115.

The process for selecting the client grid dimensions (X, Y, Z) around the leak source(s) is shown in more detail in FIGS. 1C, 1D, and 1E. A computational model is constructed as shown in FIG. 1C to estimate fluid dispersion under known leak rate and known wind direction and wind velocity. As shown in FIG. 1D, under wind velocity of 0.5 m/s, for methane leak rate of 0.5 g/s, the sensor should be placed less than ~40 ft far from the leak source. This can help the sensor to detect and measure methane concentration above ~2 ppm which is the lowest detection limit for the sensor considered here as an example. As shown in FIG. 1E, if the wind velocity is increased to 2 m/s and 5 m/s, same 0.5 g/s leak rate, due to faster dispersion, the plume dissipates quickly and is detectable at lower distances from the leak source at ~2 ppm methane concentration.

Figure 2B:
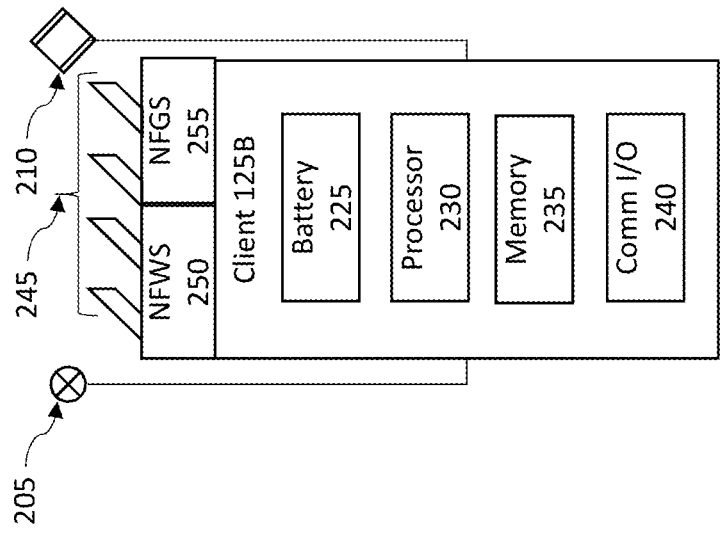
FIGS. 2A-2B are block diagrams illustrating a client device for use in a system for monitoring and detecting gas emissions.
Figure 2A:
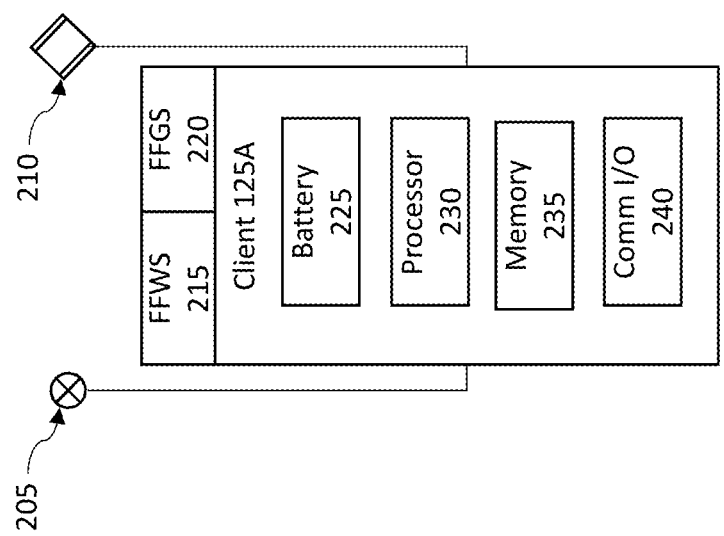

FIGS. 2A-2B are block diagrams illustrating a client device for use in a system for monitoring and detecting gas emissions. FIG. 2A is a block diagram illustrating a client computing device that can be configured as a Far-Field sensor, such as client 125A as shown and described in relation to FIG. 1. FIG. 2B is a block diagram illustrating a client computing device that can be configured as a Near-Field sensor, such client 125B as shown and described in relation to FIG. 1.

Client 125A configured as a Far-Field sensor can be located 10 to 200 feet away from a potential gas emission source 115. In some embodiments, the Far-Field sensor can be positioned 4 to 8 feet above the ground. In some embodiments, the Far-Field sensor can be positioned on the periphery or battery limits of the gas production and distribution environment 105. The Far-Field sensors, clients 125A for example, are preferably positioned to maximize the capture of gas emissions 120 and may be configured downstream of seasonally prevalent winds.

As shown in FIG. 2A, the client 125A configured as a Far-Field sensor can include a wireless communication transceiver 205. The wireless communication transceiver 205 can transmit and receive data with one or more clients 125 and with the emission analyzer 135. In some embodiments, the client 125A may also include or may alternatively include a wired communication interface (not shown). The wireless communication transceiver 205 can enable wireless data transmission of the Far-Field sensor data generated by the client 125.

As further shown in FIG. 2A, the client 125A configured as a Far-Field sensor can also include a solar panel 210. The solar panel 210 can provide a source of power for the client 125A based on converting solar energy received from the sun into electrical energy. In some embodiments, the client 125A can also include or alternatively include a configuration to receive power from a nearby AC power source, such as an electrical power grid or the like.

As further shown in FIG. 2A, the client 125A configured as a Far-Field sensor can include a Far-Field wind sensor 215. The Far-Field wind sensor 215 can include one or more sensors configured to measure a wind velocity and a wind direction. Far-Field wind sensor 215 can generate sensor data as time-series data associated with wind velocity and wind direction sensed by the Far-Field wind sensor 215 over a period of time. The time-series wind data can include data values collected every 2 seconds, every hour, every day, or every week. In some embodiments, the time-series wind data can be averaged. In some embodiments, the Far-Field sensor can include additional weather sensors which may measure ambient pressure, temperature, dew point, humidity, precipitation, and solar radiation.

The client 125A configured as a Far-Field sensor can also include a Far-Field gas sensor 220. The Far-Field gas sensor 220 can include one or more sensors configured to measure the concentration of a gas. For example, the Far-Field gas sensor 220 can be configured to measure the concentration of methane which may be present within the measurement proximity of the client 125A. Far-Field gas sensor 220 can generate sensor data as time-series data associated with gas concentrations sensed by the Far-Field gas sensor 220 over a period of time. The time-series gas concentration data can include data values collected every 2 seconds, every hour, every day, or every week. In some embodiments, the time-series gas concentration data can be averaged. In some embodiments, the Far-Field gas sensor 220 can detect common gas species including methane, ethane, propane, butane, hexane, and other hydrocarbons such as natural gas liquids (C5, C6, C8-10), mixtures of alkanes, sour gases include H2S, SOx, carbon disulfide, unsaturated HCs/petrochemicals such as ethylene, propylene, etc.

As further shown in FIG. 2A, the client 125A also includes a battery 225, a processor 230, a memory 235, and a communications interface 240. In some embodiments, the battery 225 can receive and store power generated by the solar panel 210. The processor 230 can execute computer-readable, executable instructions stored in memory 235 which when executed cause the client 125 to record sensor data received from the Far-Field wind sensor and/or the Far-Field gas sensor 220 and to store the sensor data in the memory 235. In some embodiments, the processor 230 can execute instructions to cause the client 125 to transmit the sensor data via the communications interface 240 to another client 125, and/or to the emissions analyzer 135.

As shown in FIG. 2B, client 125B can be configured as a Near-Field sensor. As a Near-Field sensor, client 125B can be located in close proximity to a potential gas emission source 115. For example, in some embodiments, the Near-Field sensor can be positioned less than 5 feet away from a potential gas emission source and preferably less than 1 foot away from the potential gas emission source. In some embodiments, the Near-Field sensor can be positioned 6 to 10 feet away from the potential gas emission source. The Near-Field sensors, clients 125B for example, are preferably positioned to maximize the capture of gas emissions 120 from an emission source 115 operating under high pressure conditions.

As shown in FIG. 2B, the client 125B configured as a Far-Field sensor or a Near-Field sensor can include a wireless communication transceiver 205. The wireless communication transceiver 205 can transmit and receive data with one or more clients 125 and with the emission analyzer 135. In some embodiments, the client 125B may also include or may alternatively include a wired communication interface (not shown). The wireless communication transceiver 205 can enable wireless data transmission of the Near-Field sensor data generated by the client 125.

As further shown in FIG. 2B, the client 125B configured as a Near-Field sensor can also include a solar panel 210. The solar panel 210 can provide a source of power for the client 125B based on converting solar energy received from the sun into electrical energy. In some embodiments, the client 125B can also include or alternatively include a configuration to receive power from a nearby AC power source, such as an electrical power grid or the like.

As further shown in FIG. 2B, the client 125B configured as a Near-Field sensor can include a Near-Field wind sensor 250. The Near-Field wind sensor 215 can include one or more sensors configured to measure a wind velocity and a wind direction. Near-Field wind sensor 250 can generate sensor data as time-series data associated with wind velocity and wind direction sensed by the Near-Field wind sensor 250 over a period of time. The time-series wind data can include data values collected every 2 seconds, every hour, every day, or every week. In some embodiments, the time-series wind data can be averaged. In some embodiments, the Near-Field sensor can include additional weather sensors which may measure ambient pressure, temperature, dew point, humidity, precipitation, and solar radiation.

The client 125B configured as a Near-Field sensor can also include a Near-Field gas sensor 255. The Near-Field gas sensor 255 can include one or more sensors configured to measure the concentration of a gas. For example, the Near-Field gas sensor 255 can be configured to measure the concentration of methane which may be present within the measurement proximity of the client 125B. Near-Field gas sensor 255 can generate sensor data as time-series data associated with gas concentrations sensed by the Near-Field gas sensor 255 over a period of time. The time-series gas concentration data can include data values collected every 2 seconds, every hour, every day, or every week. In some embodiments, the time-series gas concentration data can be averaged. In some embodiments, the Near-Field gas sensor 255 can detect common gas species including methane, ethane, propane, butane, hexane, and other hydrocarbons such as natural gas liquids (C5, C6, C8-10), mixtures of alkanes, sour gases include H2S, SOx, carbon disulfide, unsaturated HCs/petrochemicals such as ethylene, propylene, etc.

As shown in FIG. 2B, the client 125B configured as a Near-Field sensor can also include one or more baffles 245. The baffles 245 can be configured with respect to the client 125B and the components included therein so as to minimize wind advection-diffusion effects. The baffle arrangement 245 assists in maintain the Near-Field wind speed at 5 mph or less. It is preferable to position the Near-Field sensors upstream from the prevailing winds so that the angle between a vector representing the wind direction and a vector representing the distance from the leak source to the sensor is no more than five degrees.

As further shown in FIG. 2B, the client 125B also includes a battery 225, a processor 230, a memory 235, and a communications interface 240. In some embodiments, the battery 225 can receive and store power generated by the solar panel 210. The processor 230 can execute computer-readable, executable instructions stored in memory 235 which when executed cause the client 125 to record sensor data received from the Near-Field wind sensor and/or the Near-Field gas sensor 220 and to store the sensor data in the memory 235. In some embodiments, the processor 230 can execute instructions to cause the client 125 to transmit the sensor data via the communications interface 240 to another client 125, and/or to the emissions analyzer 135.

FIGS. 3A-3C are block diagrams illustrating one exemplary embodiment of a mobile platform including for use in in a system for monitoring and detecting gas emissions. As shown in FIG. 3A, a mobile platform 305, such as a CNG transport truck or a LNG transport truck can be configured to transport one or more tanks or containers 310 of a gas. The tanks 310 can terminate in and be accessed through a piping control cabinet 315 that is configured at the rear of the truck. One or more Near-Field clients can be configured in relation to the cabinet 315 in order to detect potential gas emissions that may emanate from around one or more of the tanks 310 and/or from one or more components associated with the tanks 310. For example, as shown in FIG. 3A, the truck 305 includes a first client 325A, configured as a Near-Field sensor that is positioned outside of the cabinet 315. In addition, the truck 305 includes a second client 325B, also configured as a Near-Field sensor that is positioned within the cabinet 315.

Configuring one or more clients 325 as Near-Field sensors positioned with respect to a mobile platform 305 provides advantages of detecting small leaks at the parts-per-million (ppm) scale that may emanate from inside the cabinet 315. Additionally, configuring one or more clients 325 as Near-Field sensors outside of the cabinet 315 is advantageous to detect over pressure leaks that may occur when a pressure relief device is activated. The Near-Field sensors can be configured in relation to alarms and/or leak flow recorders. The Near-Field sensors can further output data to mobile computing device, such as a smartphone or tablet with a user interface that may allow a driver of the truck to check the integrity status of one or more containers 310. The Near-Field sensors can be employed during loading or dispensing of gas (CNG) or liquid (LNG) at filling stations. In some embodiments, the clients 325 configured as Near-Field sensors with respect to a mobile platform can be configured to automatically call the nearest fire department and/or police using a wireless communication device 205 when a pressure relief device is activated. In this way, nearby communities or highways may be closed to reduce the risk of potential gas emissions associated with the tanks 310 of the mobile platform. In some embodiments, the clients 325 configured as Near-Field sensors can include an auxiliary power source, such as battery 225, the can provide continuous operation to the client 325 when the truck is parked or stationary.

FIG. 3B illustrates a configuration of tanks 310 as viewed from the rear of the truck 305. Client 325A can be configured within the cabinet 315 and client 325B can be configured inside the cabinet 315. Traditional LNG and CNG transport trailers are not equipped with active sensor devices configured to perform gas monitoring and detection due to lack of integral gas sensing and analytics model which can be used for measuring emission concentrations and further determining emission rates. As shown in FIG. 3C, each tank 310 includes a pressure relief device 320 that is routed to a top section of the cabinet 315 using piping 330. Client 325B can be configured within the cabinet 315 to detect emission leaks generated by the threaded connections coupling the pressure relief device to a tank 310. Client 325A can configured outside of the cabinet 315 to detect larger gas emissions that may occur when the pressure relief devices 320 on one or more tanks 310 are activated.

While the clients 325 are described as Near-Field sensors configured on a LNG or CNG transport truck 305, the clients 325 can also be configured on a variety of mobile platforms including rail cars or tankers and also including the mobile platforms which are not necessarily associated with the transport of a gas. For example, the clients 325 can be configured on a manned or unmanned ground vehicle capable of maneuvering to a potential gas emission source and collecting Near-Field sensor data at a location proximal to the emission source. In some embodiments, the clients 325 can be configured on a drone or a robot or on a mobile platform which can be attached to a human in motion. The Near-Field sensor data can be used to determine an emission rate associated with the emission source.

Figure 4:
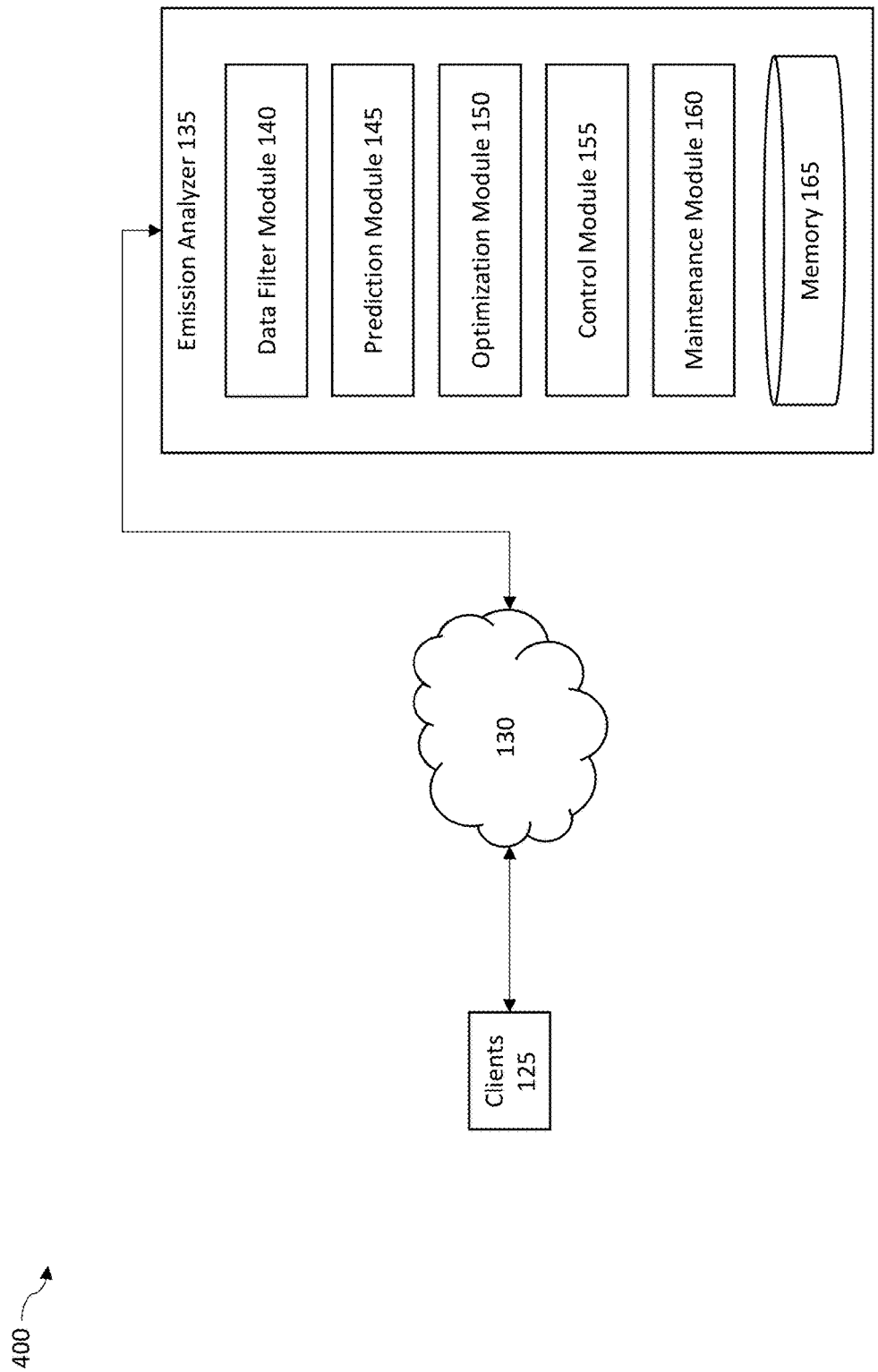
FIG. 4 is a block diagram illustrating one exemplary embodiment of an architecture of a system for monitoring and detecting gas emissions.

FIG. 4 is a block diagram illustrating one exemplary embodiment of an architecture of a system for monitoring and detecting gas emissions. As shown in FIG. 4, the system 400 includes one or more clients 125 coupled to an emission analyzer 135 via a network 130. The clients 125 can include one or more client computing devices configured as either Far-Field sensors or Near-Field sensors as described in relation to FIGS. 1-3. The clients 125 can be, for example, a large-format computing device, a small-format computing device (e.g., a smartphone or tablet), or any other similar device having appropriate processor, memory, and communications capabilities to transmit sensor and/or weather data. The clients 125 can be configured to receive, transmit, and store sensor data and/or weather data associated with determining an emission rate from a gas emission source. The clients 125 can be configured with one or more software applications. The software applications can include web-based applications as well as applications that can be directly hosted or configured on the clients 125. For example, the software applications can include technical computing applications, modeling and simulation applications, sensor control and configuration applications, emission data processing applications, and industrial asset management applications, or the like.

In some embodiments, the client devices 125 can further include a weather station configured with a plurality of weather sensing devices used to measure ambient pressure, temperature, wind speed, wind direction, humidity, and solar radiation. In some embodiments the client devices 125 can include a mobile computing device, such as a smart phone or table computing device, which may be configured to receive and provide sensor data, weather data, emission rates, emission data, or the like.

As shown in FIG. 4, the system 400 includes a network 130. The network 130 can include, for example, any one or more of a personal area network (PAN), a local area network (LAN), a campus area network (CAN), a metropolitan area network (MAN), a wide area network (WAN), a broadband network (BBN), a virtual private network (VPN), the Internet, or the like. Further, the network 130 can include, but is not limited to, any one or more of the following network topologies, including a bus network, a star network, a ring network, a mesh network, a star-bus network, tree or hierarchical network, and the like. In some embodiments, the network 130 can be a grid or sensor network formed by two or more clients 125.

As further shown in FIG. 4, the system 400 includes an emission analyzer 135 configured with a plurality of modules for determining an emission rate associated with a gas leak based on sensor data including weather data and gas concentration data. In some embodiments, one or more of the modules configured in the emission analyzer 135 can be configured on a server computing device. In some embodiments, one or more of the modules can be configured on a client device, such as client devices 125, without deviating from the spirit of the disclosure described herein.

The emission analyzer 135 includes a data filter module 140. The data filter module 140 can be configured to receive sensor data as time-series datasets from Near-Field sensors and Far-Field sensors and to filter out unusable data from the time-series datasets. The sensor data can include time-series datasets of weather data and gas concentration data collected by the Near-Field sensors and the Far-Field sensors. The data filter module 140 can receive the sensor data and automatically detect parse errors, anomalous sensor data values, incorrect dates or times, or the like. The data filter module 140 can further apply global mining to filter out data that lies outside of a sensor calibration data range associated with at least one of the clients 125.

As shown in FIG. 4, the emission analyzer 135 also includes a prediction module 145. The prediction module 145 can be configured to convert filtered gas sensor data received from the data filter module 140 to gas concentration data. The prediction module 140 can apply a transfer function to convert the filtered gas sensor data to generate gas concentration data.

The prediction module 140 can be further configured with a Near-Field advection-diffusion model expressed by equation 1 below used to determine the emission rate of a gas emission source:

$$q_0 = C(4\pi K d)\exp\left[-\frac{1}{2K}\|\bar{v}\|d(1-\cos\theta)\right] \quad (1)$$

As shown in equation 1, "C" represents the concentration of a gas in ppm (or mg/m$^3$). "d" represents the distance between a sensor and an emission source 115 in meters. "K" represents a diffusivity constant in m$^2$/s. "$\|\bar{v}\|$" represents the wind speed in meters per second, m/s. "$\theta$" represents the angle between the wind vector and the distance vector as pointed from the leak source to the sensor in radians. "$q_0$" represents the emission rate in m$^3$/s.

In predicting gas emission rates using Far-Field sensor data, the Far-Field wind data received from a client 125 configured as a Far-Field sensor and sensor location shape factors can be provided as inputs to a Far-Field model in order to generate Near-Field wind data. The Near-Field wind data and gas concentration data can then be provided as inputs to the Near-Field dispersion model described above in equation (1) to predict a gas emission rate. In some embodiments, the Far-Field model can be generated via reduced order modeling and/or via a machine learning model that has been trained using computational fluid dynamic (CFD) simulation datasets. The CFD simulation datasets represent wind vector datasets including wind velocity fields on selected Far-Field wind conditions, such as boundary conditions for a particular CFD simulation. The CFD simulation datasets also include bluff body shape factors that represent typical oil production facility object shapes. In some embodiments, the object shapes can be a cube, a horizontal cylinder, a vertical cylinder, or the like.

As further shown in FIG. 4, the emission analyzer 135 can also be configured to include an optimization module 150. The optimization module 150 can implement a polling process that will access public weather forecasting data identifying weather parameters such as precipitation probability, precipitation forecast, probability of extreme thunderstorms or high winds, relative humidity, temperature, wind speed, and wind direction to determine whether sensor data should be collected from the Near-Field and Far-Field sensors in a future period of time, such as within the next 12 hours. The optimization module 150 can further determine when the optimum time for polling or sensor data collection will occur. By recognizing patterns of wind turbulence from the weather forecasting data, the optimization module 150 can determine when weather conditions are unfavorable to receive sensor data. The optimization module 150 can determine favorable sensor polling times by calculating a Fourier spectrum of wind speed and estimating a frequency/timescale contrasting acceptable (e.g., relatively slow timescales) and unacceptable conditions (e.g., relatively fast timescales). In this way, the optimization module 150 can be configured to instruct a client device 125 to access local weather forecasting data while other nodes sleep or are otherwise inactive and can determine a window of time to conduct polling when noise in the wind sensor data is at a minimum. In some embodiments, the optimization module 150 can access the local weather forecasting data. The optimization module 150 can be configured to determine future polling windows based on the occurrence of a previously successful polling window. For example, the optimization module 150 can be configured to allow for multiple polls within an upcoming 12 hour period when polling conducted in a previous amount of time provided noise-free or noise-reduced wind data which may result from high winds, rain, or severe weather. In the event of a connection failure with a source of the public weather forecasting data, the optimization module 150 can cause one or more clients 125 to observe wind direction and speed and to poll for sensor data for a test period, such as one minute, and to halt polling in the presence of noise in the received data.

The optimization module 150 can be further be configured to post-process the gas emission rate data output from the prediction module 145 using a variety of statistical modeling methods, analytics, clustering techniques, and visualizations. For example, the optimization module 150 can apply various statistical modeling methods such as pdf, BS, C.I, and simulation. In some embodiments, timeseries data from individual sensors can be streamed to Amazon Web Servers (AWS) in real-time. The data can be comprised of raw sensor signal as it responds to local methane concentration at the location of the sensor and wind speed and direction measurements of the edge device. Sensor data sampled can be pushed to AWS every hour in a single file that requires preprocessing before getting passed on to the Bayesian inferencing model for leak rate and source location prediction. Data can be downloaded into local servers, and can be passed on to an extraction, transformation and loading (ETL) computational pipeline before being ready for the prediction algorithm. First data from all sensors can be checked for missing values and imputed where appropriate. Typically, a full dataset can be acquired unless data connectivity gets interrupted and nodes stop streaming data. Such occurrences are rare but need to be considered in any ETL. After data imputing for individual sensors, timeseries need to be synchronized due to slight variations in the time (typically less than 1 second) of measurements reported by the individual sensors. Once raw data is imputed and aligned it can be transformed into methane concentration in PPM using transfer functions. Finally, the concentration data (in PPM) can be augmented by GPS coordinates of the individual sensors and a single file encompassing the experimental time of a given experiment (typically 1 hour long) can be provided to a Bayesian inferencing model. Bayesian inversion relies on a forward model for pollutant dispersion, such as Gaussian-plume and other reduced order numerical models. Data verification and validation are essential parts of the ETL pipeline. A Python basemap (a matplotlib library extension) of the experimental setup can be displayed so we could visually verify relative sensor and source locations of a given experimental setup. This way GPS coordinates can be correctly paired with their respective sensor nodes. Any connectivity issues, signifying a node or more getting out of sync with respect to the others, can be detected programmatically by raising exceptions in case a data gap is found within the source files.

Additionally, or alternatively, the optimization module 150 can process the gas emission rate data and can apply various analytic tools such as open-source python-based libraries to construct the data pre-processing (ETL) and Statistical computing and visualization (SV) pipelines.

A summary of the different libraries along with short description is shown below in Table 1.

TABLE 1

Summary of Python Libraries used for the ETL, SV Pipelines

| Library Name | Description |
| --- | --- |
| Pymc3 | For Bayesian statistical modeling |
| Theano | For linear algebra and matrix computing |
| Pandas, Numpy, Scipy | Manipulation of timeseries data, performing database like functionality (grouping, joining . . . etc.) and common timeseries operations (resampling, shifting, slicing, rolling means, etc.) |
| Matplotlib, Scipy (stats), and Seaborn | For visualization of timeseries, histograms, probability/kernel density functions |
| Os, shutil, pickle, json | Various utilities to move data around the operating system, read/load and save data files |
| numpy.random.choice | For sampling a timeseries with replacement to construct a bootstrap |

In some embodiments, the optimization module 150 can process the gas emission rate data to perform various clustering optimizations in order to determine categories of emission rates as low/medium/high based on classifications of the gas emission rate data. Clustering methods used can include manipulation of timeseries data, performing database-like functionality such as grouping, joining, or the like, and performing common time-series data operations such as resampling, shifting, slicing, rolling means, or the like using Pandas, Numpy, or Scipy, as shown in Table 1 above.

Additionally, or alternatively, the optimization module 150 can be configured to generate a variety of visualizations based on the gas emission rate data. For example, the optimization module 150 can generate visualizations which assign a signature or finger print to each gas emission based on the determined emission rate data. For visualization of time-series data, histograms, probability/kernel density functions libraries such as Matplotlib, Scipy (stats), and Seaborn shown in Table 1 above can be used.

The emission analyzer 135 can also include a memory 165. The memory 165 can store and provide computer-readable executable instructions which when executed cause the one or more modules to perform functionality as described above. In some embodiments, the memory 165 includes a plurality of machine learning models and training data used to train the Far-Field model. The memory 165 can also store various time-series datasets associated with Far-Field wind data, Far-Field gas concentration data, Near-Field wind data, and Near-Field gas concentration data. In some embodiments, the memory 165 can store one or more rules or threshold values used in determining alarm states associated with particular gas concentrations, emission rates, weather data, and/or emission sources.

Figure 5:
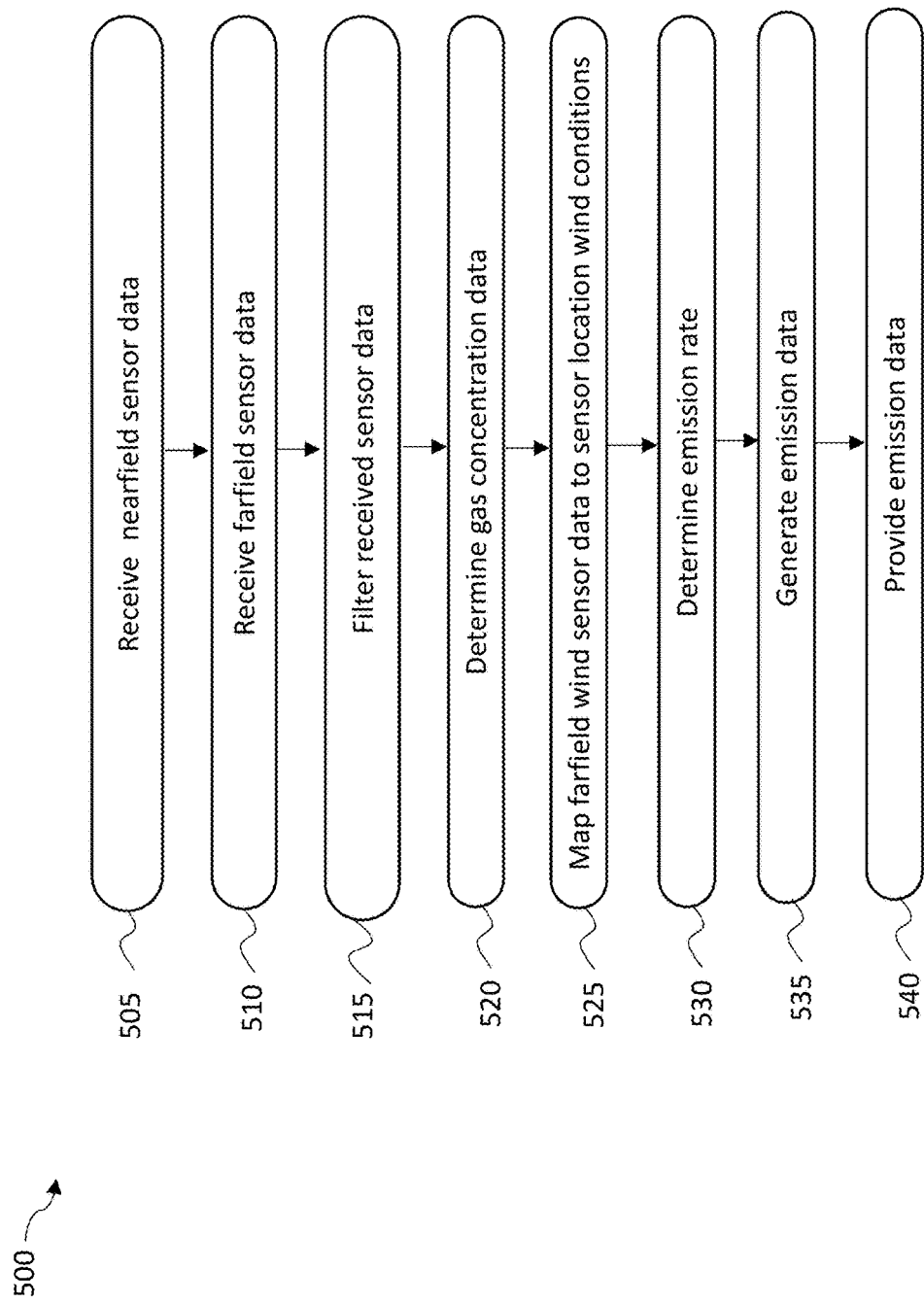
FIG. 5 is a flowchart illustrating one exemplary embodiment of a method for monitoring and detecting gas emissions using the system of FIG. 4.

FIG. 5 is a flowchart illustrating one exemplary embodiment of a method for monitoring and detecting gas emissions using the system of FIG. 4. In operation 505, Near-Field sensor data is received by the emission analyzer 135 from one or more clients 125 configured as Near-Field sensors. In operation 510, Far-Field sensor data is received by the emission analyzer 135 from one or more clients 125 configured as Near-Field sensors. In operation 515, the received sensor data is filtered by the data filter module 140 as described above in relation to FIG. 4. The data filter module 140 can perform various processing methods to cleanse the data or otherwise remove sensor data values which may be inaccurate or anomalous.

In operation 520, the prediction module 145 receives the filtered sensor data and determines gas concentration data. The gas concentration data can be determined by applying a transfer function to the filtered sensor data received from Near-Field and Far-Field sensors to determine the gas concentration data.

In operation 525, the prediction module 145 receives the filtered wind sensor data from Far-Field sensors and/or client devices 125 that can be configured as weather stations and maps the wind sensor data to sensor location wind conditions. To derive the relationship between the near-field velocity vector and the far-field sensor measurements, a data-driven modeling approach can be devised. This data-driven model can estimate the near-field wind information to be used in the dispersion model based on the data measured at the far-field wind sensor locations. To build such a model that can operate over a wide range of wind conditions, CFD models of the flow around a subset of representative infra-structures and different values of the wind vector (wind speed and directions) can be discretized over typically observed ranges of values. For example, the velocity magnitude and wind values can be parameterized over a representative range of 0.5-9.5 m/s and 0-360 degrees (every 30 degrees) for a wind sensor placed at a height of five feet. Further, to build this dataset, we assumed a square infrastructure of a standard size of 15 feet. From this ensemble of simulations, a database of input and output features corresponding to open (far) field and near-field velocity measurements can be generated for training a machine learning (ML) model. The ML architecture aims to learn a mapping in feature space using an extended basis consisting of polynomials up to order two which is similar to a shallow neural network or a single layer feed forward neural network (SLFNN). We note that learning more complex hierarchical models such as that using a deep neural network (DNN) is equally plausible but were avoided for simplicity. The data was split into training and validation datasets in a ratio of 4:1.

In operation 530, the prediction module 145 determines the emission rate associated with the received sensor data corresponding to a particular emission source. The emission rate can be determined using a Near-Field dispersion model. The Near-Field dispersion model can receive as inputs the time-series gas concentration data generated by Near-Field sensors and the Near-Field time-series wind data converted from Far-Field wind data generated by Far-Field sensors. The Far-Field wind data generated by the Far-Field sensors can be input to a Far-Field model configured to generate Near-Field wind data. The Far-Field model can receive as inputs Far-Field wind data that may be received from one or more Far-Field sensors, of that may be streamed from a remote server accessible via network 130. The Far-Field model can further receive as inputs sensor location shape factors which can be determined based on sensor installations and their location. The Near-Field dispersion model can process the inputs to determine an emission rate for a particular emission source in standard cubic feet per minute (SCFM).

In operation 535, the prediction optimization module 150 can generate emission data including the determined emission rate and one or more source locations associated with the gas emission. In some embodiments, the gas emission may not be associated with a source location. In some embodiments, the source locations can be potential source locations of the emission. The emission data can be further processed to generate additional representations of the emission rate. For example, the optimization module 150 can perform statistical modeling, apply exploratory analytics, evaluation measures, and/or clustering algorithms or methods to determine categories of emission data or emission sources based on classification techniques, as well as generating visualizations of the emission data such as emission rate signatures, emission source signatures, or the like.

In operation 540, the emission analyzer 135 can provide the emission data to one or more clients 125. The client device 125 can be configured to receive the emission data and provide it for display or store it in a memory configured on the clients 125. In some embodiments, the emission data can be provided to a control module configured to execute control instructions which can alter the operation of an emission source based on alarm conditions which may be associated with the emission data.

FIG. 6 is a block diagram of an exemplary computing device 610 suitable for use in the gas monitoring and detection system of FIGS. 1 and 4.

In broad overview, the computing device 610 includes at least one processor 650 for performing actions in accordance with instructions, and one or more memory devices 660 and/or 670 for storing instructions and data. The illustrated example computing device 610 includes one or more processors 650 in communication, via a bus 615, with memory 670 and with at least one network interface controller 620 with a network interface 625 for connecting to external devices 630, e.g., a computing device (such as client 125, emission analyzer 135, or the like). The one or more processors 650 are also in communication, via the bus 615, with each other and with any I/O devices at one or more I/O interfaces 640, and any other devices 680. The processor 650 illustrated incorporates, or is directly connected to, cache memory 660. Generally, a processor will execute instructions received from memory. In some embodiments, the computing device 610 can be configured within a cloud computing environment, a virtual or containerized computing environment, and/or a web-based microservices environment.

In more detail, the processor 650 can be any logic circuitry that processes instructions, e.g., instructions fetched from the memory 670 or cache 660. In many embodiments, the processor 650 is an embedded processor, a microprocessor unit or special purpose processor. The computing device 610 can be based on any processor, e.g., suitable digital signal processor (DSP), or set of processors, capable of operating as described herein. In some embodiments, the processor 650 can be a single core or multi-core processor. In some embodiments, the processor 650 can be composed of multiple processors.

The memory 670 can be any device suitable for storing computer readable data. The memory 670 can be a device with fixed storage or a device for reading removable storage media. Examples include all forms of non-volatile memory, media and memory devices, semiconductor memory devices (e.g., EPROM, EEPROM, SDRAM, flash memory devices, and all types of solid state memory), magnetic disks, and magneto optical disks. A computing device 610 can have any number of memory devices 670.

The cache memory 660 is generally a form of high-speed computer memory placed in close proximity to the processor 650 for fast read/write times. In some implementations, the cache memory 660 is part of, or on the same chip as, the processor 650.

The network interface controller 620 manages data exchanges via the network interface 625. The network interface controller 620 handles the physical, media access control, and data link layers of the Open Systems Interconnect (OSI) model for network communication. In some implementations, some of the network interface controller's tasks are handled by the processor 650. In some implementations, the network interface controller 620 is part of the processor 650. In some implementations, a computing device 510 has multiple network interface controllers 620. In some implementations, the network interface 625 is a connection point for a physical network link, e.g., an RJ 45 connector. In some implementations, the network interface controller 620 supports wireless network connections and an interface port 625 is a wireless transceiver. Generally, a computing device 610 exchanges data with other network devices 630, such as computing device 630, via physical or wireless links to a network interface 625. In some implementations, the network interface controller 620 implements a network protocol such as LTE, TCP/IP Ethernet, IEEE 802.11, IEEE 802.16, or the like.

The other computing devices 630 are connected to the computing device 610 via a network interface port 625. The other computing device 630 can be a peer computing device, a network device, or any other computing device with network functionality. For example, a computing device 630 can be a (client device 125 configured as a Near-Field sensor device, client device 125 configured as a Far-Field sensor device, emission analyzer 135, or the like) which may be configured within the gas monitoring and detection system illustrated in FIG. 1. In some embodiments, the computing device 630 can be a network device such as a hub, a bridge, a switch, a relay, or a router, connecting the computing device 610 to a data network such as a LAN, a WAN, the Internet, and/or a virtual private network.

In some uses, the I/O interface 640 supports an input device and/or an output device (not shown). In some uses, the input device and the output device are integrated into the same hardware, e.g., as in a touch screen. In some uses, such as in a server context, there is no I/O interface 640 or the I/O interface 640 is not used. In some uses, additional other components 680 are in communication with the computer system 610, e.g., external devices connected via a universal serial bus (USB).

The other devices 680 can include an I/O interface 640, external serial device ports, and any additional co-processors. For example, a computing device 610 can include an interface (e.g., a universal serial bus (USB) interface, or the like) for connecting input devices (e.g., a keyboard, microphone, mouse, or other pointing device), output devices (e.g., video display, speaker, refreshable Braille terminal, or printer), or additional memory devices (e.g., portable flash drive or external media drive). In some implementations an I/O device is incorporated into the computing device 610, e.g., a touch screen on a tablet device. In some implementations, a computing device 610 includes an additional device 680 such as a co-processor, e.g., a math co-processor that can assist the processor 650 with high precision or complex calculations.

The improved plume prediction system described herein addresses the technical problem of determining an emission rate of a gas emission emanating from a gas source based on received sensor data. Determining and generating accurate emission rates for different types of emission sources can be difficult and exacerbated by prevailing weather conditions. The exemplary technical effects of the methods, systems, devices, and computer-readable mediums described herein include, by way of non-limiting example, determining emission rates for expected, vented emissions as well as unexpected, fugitive emissions which may emanating from emission sources within a gas and production environment. Emission rates can be determined using a Near-Field dispersion model configured to receive wind and gas concentration data from Near-Field sensors. The Near-Field dispersion model can further be configured to receive Far-Field wind and/or gas concentration data as well as sensor location shape factors associated with objects within the gas production and distribution environment which may be located in proximity of the Near-Field or Far-Field sensor installations.

Thus the system represents an improvement of computer functionality that processes sensor data and generates emission rates and emission data corresponding to one or more types of emissions from an emission source. Additionally, the clients 125 can include an improved display or graphical user interface (GUI) that provides more efficient visualization and execution of emission data such as when visualizing the location and source of emissions. The improved GUI can also provide enhanced visualizations for alerts or notifications of gas emissions, planning maintenance or repair procedures for emission sources, or for managing production rates of the gas production and distribution environment within desirable ranges.

Certain exemplary embodiments have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in analog electronic circuitry, digital electronic circuitry, and/or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., a GPU (graphical processing unit), an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

The invention claimed is:

1. A method comprising:
   determining, by a computing system including at least one data processor, a configuration of a plurality of Near-Field sensors and a plurality of Far-Field sensors to be positioned within a gas production and distribution environment;
   positioning the plurality of Near-Field sensors and the plurality of Far-Field sensors in the gas production and distribution environment in the determined configuration, the plurality of Near-Field sensors and the plurality of Far-Field sensors including one or more wind sensors and one or more gas sensors communicatively coupled to the at least one data processor;
   receiving, by the at least one data processor, Near-Field sensor data from the plurality of Near-Field sensors and Far-Field sensor data from the plurality of Far-Field sensors, the Near-Field sensor data and Far-Field sensor data associated with a gas emission from an emission source within the gas production and distribution environment;
   determining, by the at least one data processor, gas concentration data associated with the gas emission based on the Near-Field and Far-Field sensor data;
   determining, by the at least one data processor, an emission rate corresponding to the gas emission;
   generating, by the at least one data processor, emission data corresponding to the gas emission, the emission data including the determined emission rate and one or more source locations associated with the gas emission; and
   providing the emission data.

2. The method of claim 1, wherein determining the emission rate includes providing the gas concentration data as an input to a Near-Field dispersion model.

3. The method of claim 2, wherein determining the emission rate further includes receiving Far-Field wind data as an input to the Near-Field dispersion model.

4. The method of claim 2, wherein determining the emission rate further includes determining sensor location shape factors and providing the sensor location shape factors as an input to the Near-Field dispersion model.

5. The method of claim 1, wherein the one or more sensors are positioned in a grid with respect to the gas production and distribution environment.

6. The method of claim 1, wherein the emission rate is determined based on wind data generated by the one or more wind sensors of the plurality of Near-Field sensors and/or by the one or more wind sensors of the plurality of Far-Field sensors.

7. The method of claim 6, wherein the Far-Field sensor is positioned at a height of 4 to 8 feet above the ground.

8. The method of claim 6, wherein the Far-Field sensor is positioned between 10 to 100 feet, between 30 to 100 feet, or 50 to 200 feet from a potential emission source.

9. The method of claim 6, wherein the Near-Field sensor is configured on a mobile platform.

10. The method of claim 9, wherein the mobile platform includes a manned ground vehicle, an unmanned ground vehicle, a manned aerial vehicle, an unmanned aerial vehicle, a manned surface vehicle, an unmanned surface vehicle, a robot, or a mobile platform attached to a human in motion.

11. A system comprising:
    a plurality of Near-Field sensors including one or more wind sensors and one or more gas sensors positioned in a gas production and distribution environment;
    a plurality of Far-Field sensors including one or more wind sensors and one or more gas sensors positioned in the gas production and distribution environment;
    a first computing device communicatively coupled to the plurality of Near-Field sensors and the plurality of Far-Field sensors, and including a data processor and a memory storing computer-readable instructions, the processor configured to execute the computer-readable instructions, which when executed, cause the processor to perform operations including
        receiving Near-Field sensor data and Far-Field sensor data from the plurality of Near-Field sensors and the plurality of Far-Field sensors, the sensor data associated with a gas being emitted from an emission source,
        determining gas concentration data associated with the gas emission,
        determining an emission rate corresponding to the gas emission,
        generating emission data corresponding to the gas emission, the emission data including the determined emission rate and one or more source locations associated with the gas emission, and
        providing the emission data; and a second computing device coupled to the first computing device via a network, the second computing device including a display configured to present the emission data via the display.

12. The system of claim 11, wherein the processor is further configured to determine the emission rate based on providing the gas concentration data as an input to a Near-Field dispersion model.

13. The system of claim 12, wherein the processor is further configured to determine the emission rate based on providing Far-Field wind data as an input to the Near-Field dispersion model.

14. The system of claim 12, wherein the processor is further configured to determine the emission rate based on determining sensor location shape factors and providing the sensor location shape factors as an input to the Near-Field dispersion model.

15. The system of claim 11, wherein the one or more sensors are positioned in a grid with respect to the gas production and distribution environment.

16. The system of claim 11, wherein the emission rate is determined based on wind data generated by the one or more wind sensors of the plurality of Near-Field sensors and/or by the one or more wind sensors of the plurality of Far-Field sensors.

17. The system of claim 15, wherein the Far-Field sensor is positioned between 10 to 100 feet, between 30 to 100 feet, or 50 to 200 feet from a potential emission source.

18. The system of claim 15, wherein the Near-Field sensor is configured on a mobile platform.

19. The system of claim 18, wherein the mobile platform includes a manned ground vehicle, an unmanned ground vehicle, a manned aerial vehicle, an unmanned aerial vehicle, a manned surface vehicle, an unmanned surface vehicle, a robot, or a mobile platform attached to a human in motion.

20. A non-transitory computer readable storage medium containing program instructions, which when executed by at least one data processor causes the at least one data processor to perform operations comprising:
   determining, by a first computing device, a configuration of a plurality of Near-Field sensors and a plurality of Far-Field sensors to be positioned within a gas production and distribution environment, the plurality of Near-Field sensors and the plurality of Far-Field sensors including one or more wind sensors and one or more gas sensors communicatively coupled to the first computing device;
   receiving, by the first computing device, Near-Field sensor data from the plurality of Near-Field sensors and Far-Field sensor data from the plurality of Far-Field sensors, the Near-Field sensor data and the Far-Field sensor data associated with a gas being emitted from an emission source;
   determining, by the first computing device, gas concentration data associated with the gas emission;
   generating, by the first computing device, emission data, the emission data including the determined emission rate corresponding to the gas emission and one or more source locations associated with the gas emission;
   transmitting, by the first computing device to a second computing device via a network, the emission data; and
   providing, via a display of the second computing device, the emission data for display.

* * * * *